(12) United States Patent
Nahlieli

(10) Patent No.: US 7,748,979 B2
(45) Date of Patent: Jul. 6, 2010

(54) DEVICE, SYSTEM AND METHOD FOR DENTAL TREATMENT

(75) Inventor: Oded Nahlieli, Ashkelon (IL)

(73) Assignee: Sialo-Lite Ltd., Ashkelon (IL)

(*) Notice: Subject to any disclaimer, the term of this patent is extended or adjusted under 35 U.S.C. 154(b) by 329 days.

(21) Appl. No.: 11/792,040

(22) PCT Filed: Jul. 12, 2006

(86) PCT No.: PCT/IL2006/000804

§ 371 (c)(1),
(2), (4) Date: Jun. 1, 2007

(87) PCT Pub. No.: WO2007/007331

PCT Pub. Date: Jan. 18, 2007

(65) Prior Publication Data

US 2008/0108011 A1    May 8, 2008

(30) Foreign Application Priority Data

Jul. 12, 2005    (IL) .................................. 169641

(51) Int. Cl.
*A61C 1/00* (2006.01)
(52) U.S. Cl. ..................... 433/29; 433/81; 433/216; 433/224; 433/102
(58) Field of Classification Search ............... 433/29, 433/75, 81, 102, 224, 215, 216; 600/157, 600/160, 10–16, 89
See application file for complete search history.

(56) References Cited

U.S. PATENT DOCUMENTS 3,807,048 A * 4/1974 Malmin ..................... 433/81
5,503,559 A * 4/1996 Vari ......................... 433/224
5,800,165 A * 9/1998 Kirsch et al. ................ 433/29
5,999,687 A * 12/1999 Abraham et al. ............. 385/33

(Continued)

FOREIGN PATENT DOCUMENTS

DE    44 04 983    9/1994

(Continued)

*Primary Examiner*—Cris L Rodriguez
*Assistant Examiner*—Eric Rosen
(74) *Attorney, Agent, or Firm*—The Nath Law Group; Derek Richmond; Robert T. Burnes (57) ABSTRACT

A device and system for use in a root canal treatment, the device having a probe member and a handpiece for holding the elongate probe member, the probe member having an elongate distal portion capable of being accommodated in a root canal, said probe member comprising: at least one treatment channel having a distal opening in said elongate distal portion, said at least one treatment channel being configured for enabling operation of a suitable root canal treatment tool via said distal opening; at least one illumination channel comprising a first light guide having a first proximal end configured for optical coupling to a light source system, and a second distal end in said distal portion for illuminating internal regions of the root canal during operation of said device; at least one light collection channel comprising a second light guide having a first proximal end configured for optical coupling to an imaging system, and a second distal end located in said distal portion for collecting and transmitting light reflected from internal regions of the root canal to said proximal end during operation of said device. A number of methods for monitoring and carrying out various dental treatments are provided.

58 Claims, 6 Drawing Sheets

U.S. PATENT DOCUMENTS

| | | |
|---|---|---|
| 6,013,025 A | 1/2000 | Bonne et al. |
| 6,162,052 A | 12/2000 | Kokubu |
| 6,270,342 B1 | 8/2001 | Neuberger et al. |
| 6,458,120 B1 | 10/2002 | Shen et al. |
| 6,635,011 B1 * | 10/2003 | Ozawa et al. ............... 600/178 |
| 6,679,837 B2 | 1/2004 | Daikuzono |
| 2004/0073374 A1 * | 4/2004 | Lockhart et al. .............. 702/19 |

FOREIGN PATENT DOCUMENTS

| | | |
|---|---|---|
| EP | 0 830 852 | 3/1998 |
| RU | 2 199 970 C2 | 3/2003 |

* cited by examiner

DEVICE, SYSTEM AND METHOD FOR DENTAL TREATMENT

FIELD OF THE INVENTION

This invention relates to devices, systems and methods used in dentistry in general, and in particular in the treatment of root canals.

BACKGROUND OF THE INVENTION

Conventional root canal treatment techniques are based on drilling through the top of the tooth in the case of molars, or via the lingual side or palatinal side of the tooth in the case of anterior teeth, and removing the infected pulp. The root canal is then subjected to several therapeutic procedures including extirpation of the root pulp, cleaning and clearing the canal, widening the canal and smoothing its walls by removing hard tissue obstacles, treating it to remove infection pathogens, washing, drying and filling. One or more x-rays of the root are required to provide feedback on the process. Dental drills and endodontic files are commonly employed for at least some of these procedures. Lasers are known for use in general surgery and dentistry, and are sometimes employed for the material removing process.

For example, U.S. Pat. No. 6,162,052 discloses a laser handpiece configured by a main body and a laser probe mounted on the tip end of the main body. The laser probe has an emission fiber, and a laser beam generated by a laser beam source is emitted from an emission end portion of the emission fiber. The emission end portion of the emission fiber is formed into a circular conical shape. The laser beam emitted from the emission end portion contains a first laser beam which is emitted in the axial direction of the emission fiber, and a second laser beam which is emitted in a ring-like shape in a radial direction of the emission fiber.

U.S. Pat. No. 6,458,120 discloses a surgical laser system combining a laser diode array remotely connected to a hand-held surgical probe by a fiber bundle. The surgical probe includes a laser head which produces a laser beam for surgical tissue ablation that is delivered through a disposable intraocular probe tip. The probe tip is made of a short section of optical fiber. Auxiliary water and thermal electric cooling integral to the hand piece cools the laser head.

U.S. Pat. No. 6,679,837 discloses a medical surgical or dental laser light irradiating apparatus which enables operators as well as third persons to view the treatment. The medical laser light irradiating apparatus includes an optical fiber for emitting from its front end the laser light, a handpiece for holding said optical fiber, a relatively large camera and light incident face which is made integrally with the handpiece so that it faces at least a laser light irradiated area and is spaced therefrom, imaging means for imaging of at least laser light irradiated area based upon the light which is received through the light incident face, display means for displaying a result of imaging from said imaging means, and jetting means for jetting an air to an area in front of said light incident face. By way of general background, other imaging systems are known, for example in U.S. Pat. No. 6,013,025, which discloses a miniaturized endoscope formed by passing light in both directions down the endoscope.

SUMMARY OF THE INVENTION

According to one aspect of the invention, a device is provided for use in a root canal treatment, the device comprising: a probe member and a handpiece for holding said elongate probe member, said probe member having an elongate distal portion capable of being accommodated in a root canal, said probe member comprising:

at least one treatment channel having a distal opening in said elongate distal portion, said at least one treatment channel being configured for enabling operation of a suitable root canal treatment tool via said distal opening;

at least one illumination channel comprising a first light guide having a first proximal end configured for optical coupling to a light source system, and a second distal end in said distal portion for illuminating internal regions of the root canal during operation of said device;

at least one light collection channel comprising a second light guide having a first proximal end configured for optical coupling to an imaging system, and a second distal end located in said distal portion for collecting and transmitting light reflected from internal regions of the root canal to said proximal end during operation of said device.

The said elongate distal portion may comprise a length dimension along an elongate direction generally correlated with a depth of a root canal, and the length dimension may be, for example, between about 10 mm and about 30 mm. The elongate distal portion may comprises a distal tip having a transverse dimension in a direction orthogonal to said elongate direction generally smaller than a width of a root canal at the apex thereof. The elongate distal portion may comprise a said transverse dimension that is generally uniform along said elongate dimension thereof. For example, the transverse dimension may be between about 0.5 mm and about 1.5 mm. Alternatively, the elongate distal portion comprises a said transverse dimension that varies along said elongate dimension thereof. For example, the transverse dimension may vary between about 0.5 mm and about 1.5 mm along said elongate dimension thereof.

Optionally, the distal opening, the distal end of said first light guide, and the distal end of said second light guide are at or proximate to said distal tip. Optionally, the elongate distal portion has an enlarged portion proximately spaced from said tip by a first spacing, and the first spacing may comprise a length dimension along an elongate direction generally correlated with between about 50% and about 70% of a depth of a root canal including the tip thereof. In such an embodiment, the distal opening and said distal end of said first light guide may be at or proximate to said distal tip, and the distal end of said second light guide may be comprised in said enlarged portion. Alternatively, the distal opening may be at or proximate to said distal tip, and the distal end of said first light guide and said distal end of said second light guide are comprised in said enlarged portion.

The treatment channel may comprise a suitable bore adapted for accommodating and enabling operation of any one of: a laser tool, a dental drill, a dental file, an ultrasonic tool, an RHF cutting tool, a reaming tool, a grasping tool, a syringe needle or the like. Optionally, the treatment channel is substantially rectilinear and comprises a proximal opening in said device substantially longitudinally opposed to said distal opening.

The device may optionally comprise the light source system optically coupled to said first light guide. The light system may optionally comprise at least one LED, for example.

Optionally, the first light guide comprises at least one of: at least one optical fiber; any suitable optical waveguide arrangement.

The device may optionally comprise the imaging system optically coupled to said second light guide. Optionally, the imaging system comprises a CCD or the like in optical communication with said distal end of said second light guide via a system of lenses. The CCD or the like may be operatively connectable to a microprocessor unit or the like adapted for processing images transmitted thereto by said CCD or the like. Optionally, the second light guide comprises an optical folding member.

Alternatively, the second light guide comprises at least one optical fiber.

Optionally, the at least one illumination channel is integral with said at least one light collection channel, said corresponding first waveguide being integral with said second light collection channel.

The device may optionally comprise at least one auxiliary channel having a first proximal end configured for operative connection to at least one of a fluid source and a vacuum source, and a second distal end in said distal portion for providing fluid or a vacuum, respectively, to internal regions of the root canal during operation of said device. For example, the fluid source may comprise any one of a liquid or air source.

Optionally, the handpiece comprises a longitudinal axis set an angle α with respect to a longitudinal axis of said probing member. By way of example, angle α may be between about 45° and about 135°.

According to another aspect of the invention, a system for root canal treatment is provided, comprising a device according to the first aspect of the invention, comprising any combination of features therein;

a light source system coupled to said proximal end of said first illumination system;

an imaging system coupled to said proximal end of said second illumination system;

a root canal treatment tool comprised in said treatment channel, said tool having a treating portion associated with said distal outlet.

The tool may comprise, for example, any one of: a laser tool, a dental drill, a dental file, an ultrasonic tool, an RHF cutting tool, a reaming tool, a grasping tool, a syringe needle or the like. Optionally, the tool is a laser tool having a laser transmission end adapted for any one of axial transmission of a laser beam and non-axial transmission of a laser beam, with respect to a longitudinal axis of said elongate distal portion. Alternatively, the tool is a syringe needle coupled to at least one of a source of filling agent and a source of sealing agent for respectively filling or sealing a root canal during operation of the device.

According to another aspect of the invention a method is provided for monitoring a root canal treatment, comprising:

illuminating the root canal with an illumination radiation and acquiring at least one image of said root canal illuminated thereby, in association with a root canal treatment.

Optionally, the illumination and image acquisition are carried out by means of a suitable probe member inserted into said root canal. This may optionally be carried out using the system according to the second aspect of the invention.

Optionally, the image acquisition may be carried out while performing a root canal treatment.

Optionally a plurality of images may be acquired to provide a video stream in real time.

According to another aspect of the invention, a method is provided for treating a root canal, comprising illuminating the root canal with an illumination radiation and acquiring at least one image of said root canal illuminated thereby; and performing a root canal treatment.

The image acquisition may be carried out while performing a root canal treatment. Optionally, a plurality of images is acquired to provide a video stream in real time. Optionally, illumination and said image acquisition may be carried out by means of suitable probe member inserted into said root canal. Optionally, the method may be carried out using a system according to the second aspect of the invention. Optionally, the root canal treatment may comprise one of a sealing or filing procedure for the root canal. Optionally, said one of a sealing or filing procedure comprises injecting a suitable sealant or filler, respectively, to the root canal via said treatment channel.

BRIEF DESCRIPTION OF THE DRAWINGS

In order to understand the invention and to see how it may be carried out in practice, some embodiments will now be described, by way of non-limiting example only, with reference to the accompanying drawings, in which.

DETAILED DESCRIPTION OF EMBODIMENTS

Figure 1:
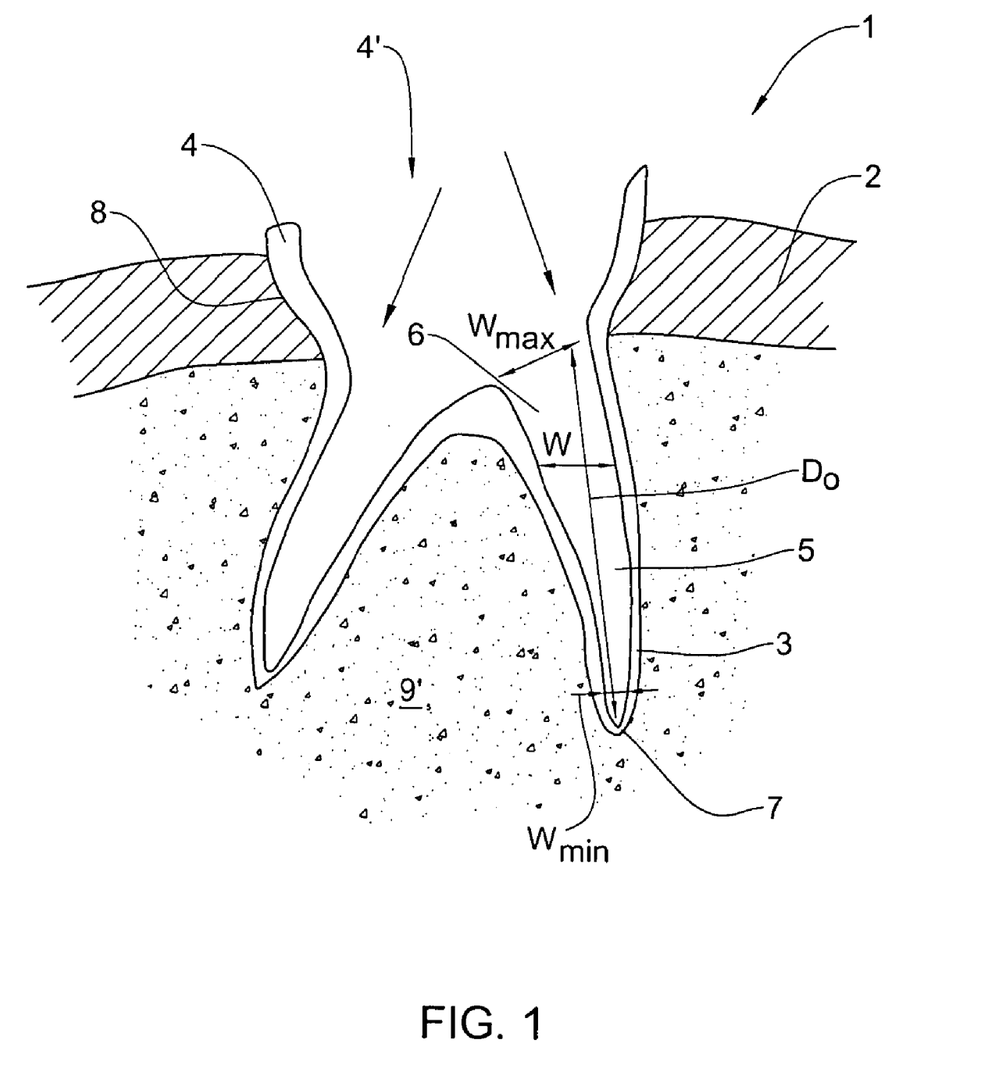
FIG. 1 schematically illustrates the general anatomy of a tooth including a root canal.

FIG. 1 illustrates the general anatomy of a tooth 1 such as a molar that is being prepared for a root canal treatment. Part of the crown 4 is removed by drilling or using any other suitable technique, for example, followed by removal of pulp so that only dentine 3 remains surrounding the root canal 5. The root 6 comprises a root apex 7 that projects into the jaw 9'. The root canal 5 comprises a depth $D_0$, which may be regarded as the linear length of the root 6 between the neck 8 of the tooth and the root apex 7, and width W which is typically the same or greater than the original diameter or width of the pulp space that is left when the pulp is removed therefrom. The width W typically diminishes in magnitude from a maximum diameter or width $W_{max}$ the root opening 6 to a minimum diameter or width $W_{min}$ at the root apex 7, and thus the width W may be regarded as an average or median value, for example, of the root canal width or diameter for a given root canal.

Figures 2, 3:
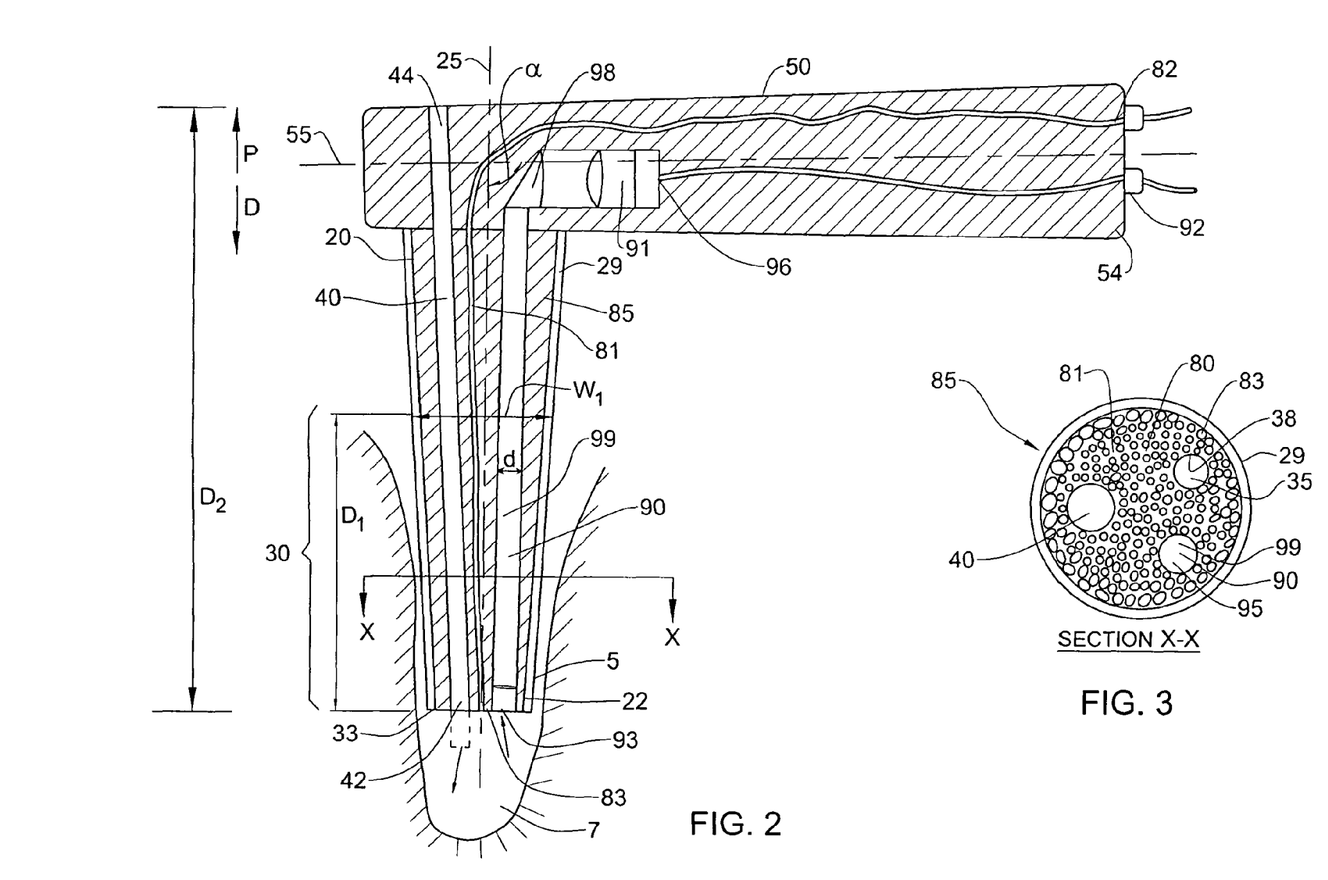
FIG. 2 illustrates, in transverse cross-sectional view, a device according to one embodiment of the invention.
FIG. 3 illustrates a longitudinal section of the embodiment of FIG. 2, taken along X-X.

Referring to FIGS. 2 and 3, a device for use in a root canal treatment according to a first embodiment of the invention, generally designated 100, comprises an elongate probe member 20, and a handle or handpiece 50 for holding the probe member 20.

Herein the term "distal" (D) relates to a direction generally towards the root apex 7, or away from the user of the device, while the term "proximal" (P) refers to a direction opposed to distal, that is, a direction generally away from the root and towards the root opening or crown, or towards the user of the device.

The probing member 20 comprises an elongate distal portion 30 that is capable of being inserted and accommodated in at least a part of a root canal 5 for operation of the device 100. Accordingly, the elongate distal portion has an axial dimension $D_1$ in the distal direction that is generally correlated to the depth into which it is desired to insert the probe member 20 with respect to the root canal, and may be as deep as the depth $D_0$, of the root canal 5. Dimension $D_1$ thus may be of similar or smaller dimension to $D_0$. Thus, for some applications of the device it is possible for the axial dimension $D_1$ to be smaller than the depth $D_0$, for example when the specific root canal tool being used (see below) has an effecting working depth that projects beyond the probe distal tip 22 towards the root apex 7.

While the depth $D_0$, may vary between individuals, and from tooth to tooth in any individual, between different roots of a single tooth, and further depend also on the age, sex and physical makeup of the individual among other factors, the depth $D_0$, may vary in most cases between about 15 mm and about 30 mm.

The shape and transverse dimension or width $W_1$ of the distal portion 30 may be uniform or may vary. For example, the distal portion 30 may be in the form of an elongate cylinder, the diameter or width $W_1$ being smaller than the corresponding width W of the root canal 5 at the depth to which is desired to introduce the probe member 20, to allow the distal portion 30 to be inserted therein with some clearance. Thus, if it is desired that the distal portion should be inserted to the root apex 7, then the diameter $W_1$ should be a little under the minimum width $W_{min}$ of the root canal 5. In such a case, $W_i$ may be, by way of example, between about 300 micron to about 500 micron or to about 700 micron, depending on the actual dimensions of the root canal with respect to which the device is being used. Alternatively, it may be sufficient for the distal portion to be introduced to between about 50% and about 70% or about 80% of the depth $D_0$ towards the apex 7, in which case $W_1$ may be, by way of example, between about 500 micron and about 700 microns or more, depending on the actual dimensions of the root canal with respect to which the device is being used. Alternatively, it may be sufficient for the distal portion to be introduced to between about 20% and about 35% or about 45% of the depth $D_0$ towards the apex 7, in which case $W_1$ may be, by way of example, between about 700 micron and about 1300 micron or about 1500 micron, depending on the actual dimensions of the root canal with respect to which the device is being used.

Alternatively, the distal portion may be in the form of an elongate frusto-cone, having a maximum diameter or width and a minimum diameter of width such as to enable the probe to be introduced to the desired depth into the root canal 5 while providing a lateral clearance therebetween. Thus, if it is desired that the distal portion 30 should be inserted to the root apex 7, then the minimum diameter at the distal end of the probe member 20 should be a little under the minimum width $W_{min}$ of the root canal 5, and the maximum diameter of the probe, at the proximal end of the distal portion 30, should also be less than the width $W_{max}$. The same applies, mutatis mutandis, when it is desired to limit the depth of insertion of the probe to less than up to the apex.

The mean or median width W typically varies between individuals, and from tooth to tooth in any individual, and within a tooth having multiple roots, and further depends also on the age, sex and physical makeup of the individual, among other factors.

The longitudinal dimension $D_2$ of the probe member 20, including the part of the handpiece 50 to which the probe member is connected, is such as to enable the device 100 to be inserted and manipulated in the oral cavity, and allow the distal portion 30 to be inserted towards and into the root canal 5.

The probe member 20 may be rigid or semi rigid, having at least sufficient rigidity to enable the same to be manipulated into the root canal by handling the handpiece 50. The probe member 20 may thus be made from a suitable metal or hard plastic material, for example.

A longitudinal axis 25 may be defined for the probe member 20, taken along the elongate direction thereof. The hand piece 50 is configured for enabling the user to hold and manipulate the probe member 20, and may also comprise an elongate graspable member having its longitudinal axis 55 at an angle α to axis 25. Angle α may have any suitable angular value, by way of non-limiting example in the range of from about 45° and about 135°, including for example about 90° or about 125°, inter alia. In other embodiments, the angle may be about 0°, and thus the handpiece 50 may be in the form of as a wand.

In the illustrated embodiment, the angle α is fixed, though in other embodiments, this angle may be variable, the device 100 comprising a suitable pivoting or deflection mechanism (not shown) for rotating or bending the probe member 20 with respect to the handpiece 50, allowing the user greater flexibility in use of the device 100. The probe member 20 and the hand piece 50 may be integrally or otherwise joined to one another.

The device 100, and in particular the probe member 20, comprises at least one treatment channel 40 having a distal opening 42 at the tip of the distal portion 30, and the treatment channel 40 allows access to a tool, collectively designated as 150 (FIG. 9) to operate on the root canal. In the illustrated embodiment the treatment channel is in the form of an elongate bore having a proximal opening 44 longitudinally opposed to the distal opening. By way of non-limiting example, the bore may comprise a diameter of between about 200 micron and about 500 micron. The proximal opening 44 allows any suitably shaped tool, in particular a rigid or semi rigid elongate tool, to be inserted into the treatment channel 40 such that a distal working end of the tool may be projected into the root canal 5 via the distal opening 42. Such a tool, for example a dental file or reamer, which may be made from nickel titanium or stainless steel for example, may be operated manually from outside of the proximal opening 44.

Other tools, each of which may be used in turn via the working channel 40, may include, by way of non-limiting example, a laser energy delivery system, such as a laser cutting tool, a grasping tool such as micro tongs or a magnetized grasping tool, inter alia.

Figure 4:
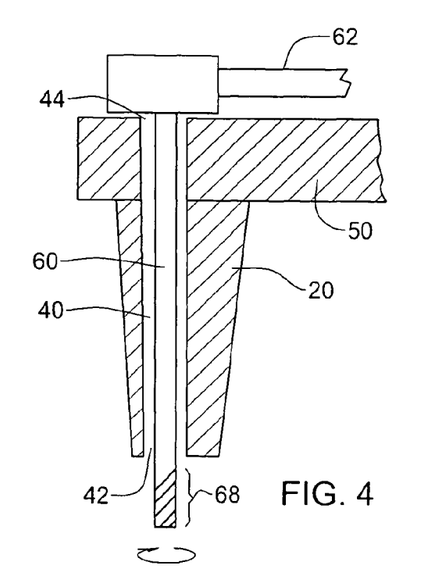
FIG. 4 illustrates in partial transverse cross sectional view the embodiment of FIG. 2 comprising a tool.

Alternatively, and referring to FIG. 4, such a tool 60 may be a powered tool, for example a dental drill or reamer, and the motor housing and handpiece 62 of the tool may be reversibly or permanently mounted onto the device 100 for use therewith. Such drills may comprise, for example, diamond drills or tungsten drills, and may be used for removing the crown, for example. The working portion 68 of the tool, i.e. the portion of the tool that interacts with the root canal or other dental tissues, projects distally into the root canal 5 from the distal end of the distal portion 30.

Alternatively, the tool may comprise a syringe having a syringe needle of suitable dimensions that may be inserted into the working channel 40 and optionally extend therethrough such that the tip of the syringe projects from the opening 42, and enables a desired agent to be delivered to the root via the syringe. Such an agent may comprise, by way of non-limiting example, irrigating solutions, antibiotics, liquid filler, liquid sealant, and so on, inter alia.

Figure 5:
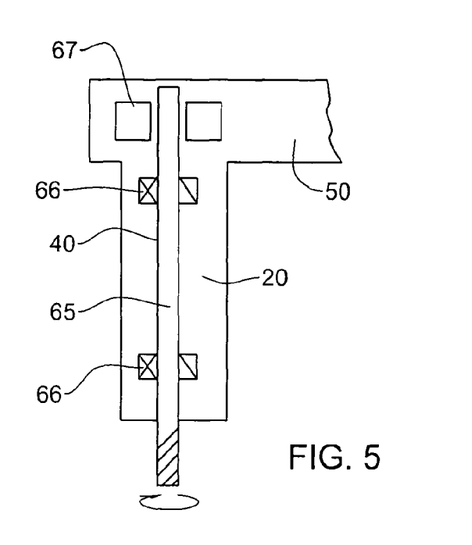
FIG. 5 illustrates in partial transverse cross sectional view a variation of the embodiment of FIG. 2 comprising an integral tool.

Alternatively, and as illustrated in FIG. 5, a powered tool 65 may be integrated with the device 100, comprising suitable bearings 66 and a suitably powered micromotor 67.

In some variations of this embodiment, the treatment channel may be adapted for accommodating and allowing operation of a non-elongate tool or for a tool that does not require access via the proximal opening 44, and thus this opening may be omitted in such an embodiment.

Figures 6, 6A:
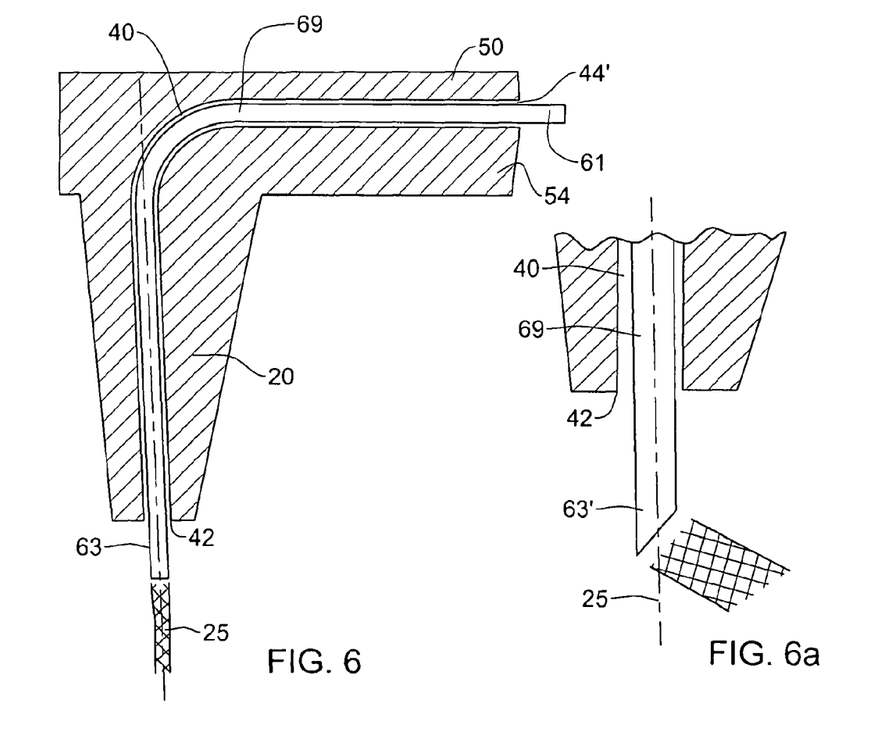
FIG. 6 illustrates in transverse cross sectional view a variation of the embodiment of FIG. 2 comprising a non-rigid tool.
FIG. 6a illustrates a variation in the tool of FIG. 6.

For example, the tool may comprise a dental laser tool, and such tools are well known in the art. Referring to FIG. 6, for example, the treatment channel 40 may extend to the user end 54 of the handpiece 50, at the proximal opening 44' thereat, and allow a suitable laser light guide, such as for example one or a plurality of suitable fibers 69, to be passed through the treatment channel 40 to the distal opening 42 and to pass therethrough. (Alternatively it may also be possible to route the fibers 69 via proximal opening 4' when used with the embodiment of FIG. 2.) The proximal end 61 of the optical fiber(s) 69 is optically coupled to a suitable laser radiation generator, for example an Erbium laser light source, via suitable optical couplers. Alternatively, the optical fibers 69 may be provided in the elongate treatment channel 40 of the embodiment of FIG. 2, via the proximal opening 44. Alternatively, the laser tool may comprise a hollow wave guide, coupled to the laser source, and sealed at the distal end 63 by a sapphire tip, which is shaped to direct the laser radiation in the required direction to the area to be treated, for example axially as illustrated in FIG. 6, or at an angle to axis 25, as illustrated in FIG. 6a, where the distal end 63' is wedge-shaped at a suitable wedge angle. Such a hollow wave guide may be, by way of example, of diameter about 100 micron to about 160 micron.

Figure 7:
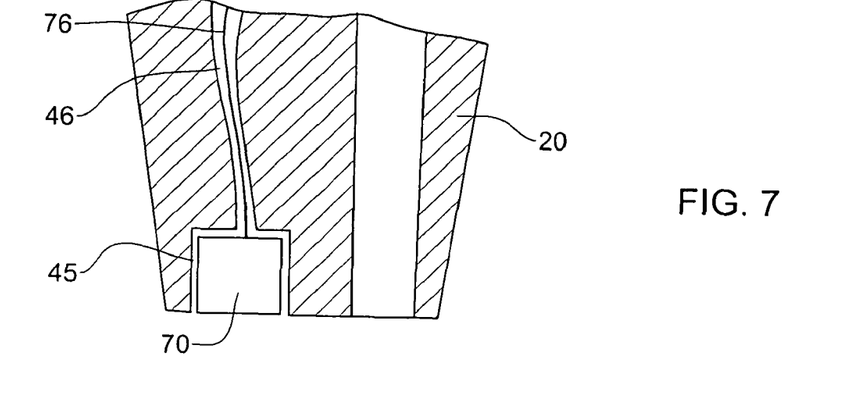
FIG. 7 illustrates in partial transverse cross sectional view another variation of the embodiment of FIG. 2 comprising a tool.

In another example, and referring to FIG. 7, the required tool for root canal treatment may be an ultrasonic tool or an RHF cutting tool, collectively referred to as treatment tool 70, wherein, the treatment channel 40 comprises a recess 45 for accommodating the tool, and a cable channel 46 for passing the cables 76, that provide power and control to the treatment tool 70, between the treatment tool 70 and the user end 54 of the device 100, to be connected from there to a suitable power and control system.

Ultrasonic cutting tools are known in the art and may comprise, for example, a piezo electric or electromagnetic source for providing the high energy vibrations required for operation of the tool. Some examples of such ultrasonic cutting tools may include: the Enac device, produced by Osada (Japan); the Satalec device, produced by Acteon Group, (France); the EMS ultrasonic device, produced by EMS (Switzerland); the Varios 750 device, by NSK (Japan); the Miniendo II device produced by Sybron Dental (USA).

RHF cutting tools are also known, for example diathermic devices (monopolar, bipolar, RHF) and can be used for cutting through dental soft tissues. By way of non limiting example, such a device may include the "Erbotom 80" device, produced by ERBE (Germany).

In some embodiments of the invention, several treatment channels may be provided, of the same or different types of treatment channels.

Referring again to FIGS. 2 and 3, the device 100 further comprises an illumination channel 85, comprising a light guide 80, for illuminating the internal regions of the root canal during operation of the device 100. Light guide 80 may be in the form of a plurality of optical fibers 81 (only one fiber is schematically illustrated in FIG. 2) accommodated within the shell 29 of the probe member 20, having a proximal end 82 configured for optical coupling to a suitable light source system 200 (FIG. 9), and a distal end 83 in distal portion 30 via which illuminating light from the light source is transmitted to the internal regions of the root canal during operation of said device. Thus, the light guide 80 may comprise a multi-fiber wave guide, having, by way of non-limiting example, a diameter of between about 300 micron to about 350 micron accommodating about 3000 optical fibers or more. The distal end 83 of the fibers may be optically coupled to a suitable lens for focusing the illumination light to any desired part of the internal regions of the root canal.

Alternatively, the illumination channel may comprise a suitable hollow wave guide optically coupled to one or more LED's, which may optionally be accommodated in the device 100. The LED's may be powered by a suitable power source, e.g. batteries, in the device 100, and/or via an external power source via suitable connectors.

Optionally, a plurality of illumination channels may be provided.

Referring again to FIGS. 2 and 3, the device 100 further comprises a light collection channel 95, comprising a light guide 90, for acquiring images of the internal regions of the root canal illuminated by the illuminating channel 85. In the illustrated embodiment, the light guide 90 comprises a lumen 99 having a proximal end 92, equipped with suitable lenses, configured for optical coupling to an imaging system 96, such as for example a CCD, and a distal end 93, also equipped with suitable lenses, located in said distal portion 30 for collecting and transmitting light reflected from internal regions of the root canal to the proximal end 92 during operation of said device. In the illustrated embodiment, the imaging system 96 is housed in the hand piece 50 and has its optical axis generally aligned with axis 55, and a suitable optical folding arrangement, such as a mirror or prism 98, may be used to direct light collected from the internal regions of the root canal via distal end 93 to the imaging system 96. Image data collected by the imaging system 96 may be communicated to a suitable image analysis and display unit 300 (FIG. 9), for example a computer, for analysis and display. The imaging system 96 may provide discrete images of the said internal surfaces as required, or may provide a sequence of such images in real time providing a video stream that may be viewed by the user of the device and/or any other observer. Optionally, such images may also be recorded in a memory or any suitable recording device. Alternatively, the imaging system 96 may be a video camera.

Alternatively, the imaging system 96 may be accommodated in the probe member 20, or indeed the handle piece 50, but having its optical axis generally aligned with axis 25, and thus the optical folding arrangement illustrated in FIG. 2 may be omitted from the lumen 99.

By way of non-limiting example, the diameter d of lumen 99 may be from about 300 micron to about 1000 micron.

Alternatively, the light guide 90 may be in the form of a plurality of optical fibers accommodated within the shell 29 of the probe member 20, having a proximal end configured for optical coupling to a suitable imaging system via an optical connector at the user end 54 of the device 100, and having a distal end in distal portion. Thus, the light guide 80 may comprise a multi-fiber wave guide, having, by way of non-limiting example, about 3000 to about 6000 optical fibers. The distal end of the fibers may be optically coupled to a suitable lens for focusing into the fibers the light reflected from the illuminated internal regions of the root canal.

Optionally, a plurality of light collection channels may be provided.

Figure 9:
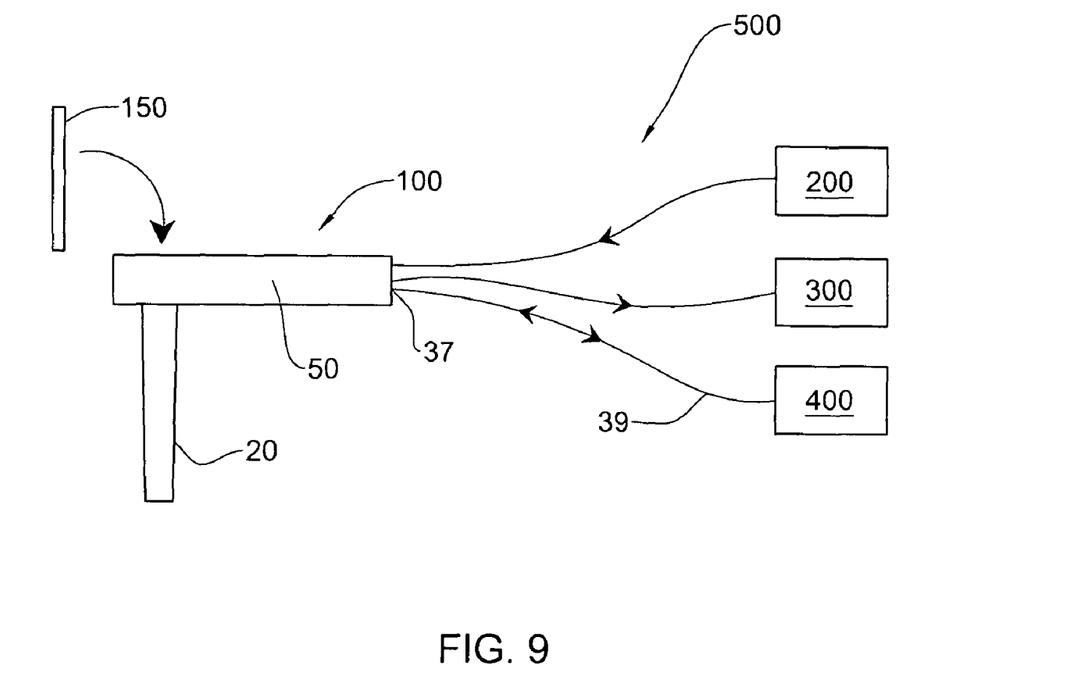
FIG. 9 illustrates schematically a system according to one embodiment of the invention.

Referring to FIGS. 3 and 9 in particular, the device may further optionally comprise at least one auxiliary channel 35 having a proximal end 37 configured for operative connection to at least one of a fluid source and a vacuum source, collectively designated herein at 400, via fluid or vacuum line 39. The auxiliary channel 35, in the lumen 38, further comprises a distal end in said distal portion 30 for providing fluid or a vacuum, respectively, to internal regions of the root canal during operation of said device. The fluid may be pressurised air or a lubricating, sterilizing or washing liquid, for example, and the vacuum provided by the source 400 allows the treated area to be drained. The lumen 38 may comprise an internal diameter of about 50 micron to about 70 microns, by way of non-limiting example.

By way of non-limiting example, the diameter of auxiliary channel 35 may be between about 55 micron and about 75 micron.

In the embodiment illustrated in FIGS. 2 and 3, the treatment channel 40 and the lumens 99 and 38 are each defined by suitable tubes (not shown) enclosed in a cylindrical shell 29, and the space between the inner surface of the shell 29 and the outer surface of the tubes comprises a plurality of fibers 81 of the illuminating channel 85. Furthermore, the distal ends 42, 93, 83 of the treatment channel, the light collection channel 95, and the illumination channel 85, respectively, are all comprised at the distal end 33 of the distal portion 30, and thus the width $W_1$ of the distal end 33 must be sufficiently narrow to allow the distal portion 30 to be inserted into a desired depth with respect to a particular root canal, for example up to about a third, up to about two thirds or up to substantially the full depth of the canal towards the apex. Alternatively, the illumination channel and the light collection channel may be integral one with the other, and comprise a plurality of optical fibers, wherein some of the fibers are used for illumination, while others are used for image acquisition.

By way of non-limiting examples: the diameter $W_1$ of the probe member 20, in particular of the distal portion 30, may be between about 300 micron and about 1500 micron; axial length $D_1$ of the distal portion 30 may be between about 15 mm and about 30 mm, or between 18 mm and about 25 mm, or between 10 mm and 15 mm, and the particular range may depend on the depth of the root canal being treated or monitored, and the penetration desired into the root canal; the longitudinal dimension $D_2$ of the probe member 20 may be between about 15 mm and about 30 mm, or between 18 mm and about 25 mm, or between 10 mm and 15 mm, and the particular range may depend on the depth of the root canal being treated or monitored, and the penetration desired into the root canal.

Other arrangements are of course possible.

Figure 8A:
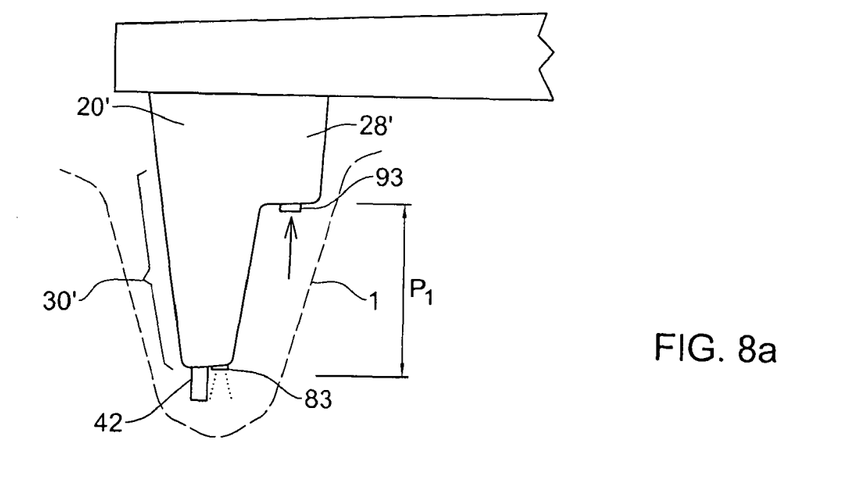
FIGS. 8a and 8b illustrate in partial transverse cross sectional view a number of variations of the probe member of the embodiment of FIG. 2.

For example, referring to FIG. 8*a*, in a modified probe member 20' the distal ends 42 and 83 of the treatment channel and the illumination channel 85, respectively, are comprised at the distal end 33 of the distal portion 30, while the distal end 93 of the light collection channel 95 is comprised on an enlarged portion 28' of the probe member 20'. The distal portion 30' of the modified probe member 20' comprises the distal end 93, and the enlarged portion 28' is spaced from the tip or distal end 33 of the probe member 20' by a dimension $P_1$, allowing the diameter of the probe member 20' distal from the enlarged portion to be narrower than at the enlarged portion, which may have the same diameter as that of the distal end 33 of the embodiment of FIG. 2, for example. Thus, the geometry of the distal portion 30 may take advantage of the relatively wider root width at the neck, while maximizing the size of the treatment channel 40 and illumination channel 85.

Figure 8B:
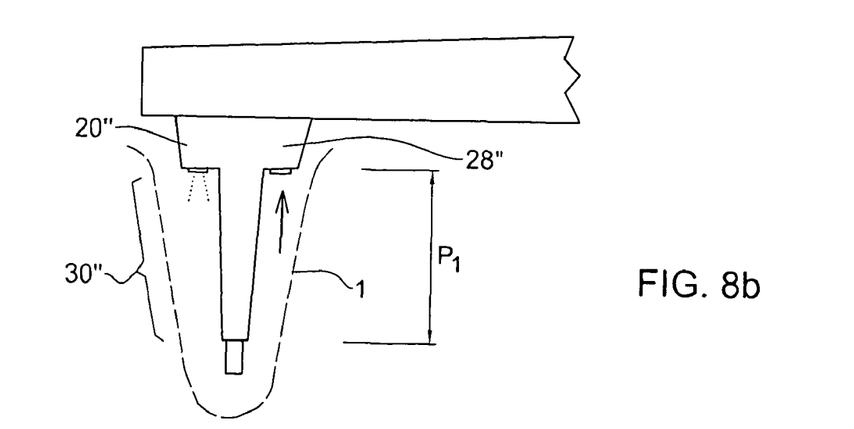

In another example illustrated in FIG. 8*b*, a modified probe member 20" comprises the distal end 42 of the treatment channel at the distal end 33 of the distal portion 30, while the distal ends 83, 93 of the illumination channel 85 and the light collection channel 95, respectively, are comprised on an enlarged portion 28" of the probe member 20". The distal portion 30" of the modified probe member 20" comprises the distal ends 83, 93, and the enlarged portion 28" is spaced from the tip or distal end 33 of the probe member 20" by a dimension $P_1$, allowing the diameter of the probe member 20" distal from the enlarged portion to be narrower than at the enlarged portion, which may have the same diameter as that of the distal end 33 of the embodiment of FIG. 2, for example. Thus, the geometry of the distal portion 30 may take advantage of the relatively wider root width at the neck, while maximizing the size of the treatment channel 40 even more than in the example of FIG. 8*a*.

Dimension $P_1$ may be, by way of example, between about 50% and about 70% of the dimension $D_1$ of the distal portion 30.

The device 100 can therefore form part of a system for treating a root canal comprising, in addition to said device 100, at least one of: an illumination source 200 operatively connected to the illumination channel 85; an image analysis and display system 300 operatively connected to the light collection channel 95; a fluid and/or vacuum system 400 operatively connected to the auxiliary channel 35; and a suitable tool 150.

The device 100 may be fully disposable, i.e., may be made from materials that render the device disposable after use with one patient or that permit such disposability from an economic perspective, for example. Alternatively the probe member or at least the distal portion thereof are disposable, and are releasably connected to the hand piece 50 or the remainder of the probe member, respectively, in a suitable manner. Alternatively, the device, or the probe member, or at least the distal portion thereof, may be provided with a suitable sheath (not shown) for protecting the device from contamination during use, and the sheath is disposed of after use with a patient.

Alternatively, the device 100 may be sterilizable, for example by autoclaving, and components thereof sensitive to such sterilization are removable therefrom prior to any such operation.

The device 100 and system 500 of the invention may be operated in a number of ways.

Monitor Mode

In monitor mode, the device 100 is used only as an endoscope, for monitoring the state of the tooth, and of a root canal for example, for providing visual data thereof. This can assist the dental practitioner such as the dentist to plan and execute a root canal treatment or other treatment in the oral cavity, or other body parts. In operation, the illumination source is switched on to illuminate the dental or other surfaces that it is desired to inspect, via the illumination channel 85, and the light collection channel 95 picks up light reflected from these surfaces and displays the same in the optical display system 300. The configuration of the distal portion 30, in particular its narrow and elongate dimensions are such as to allow the distal end 93 to be within the narrow confines of a root canal so that this may be directly imaged by the system 300, and thus the user and/or other parties.

Root Canal Treatment Mode

In this mode, the device is used as a root canal treatment device with the capability of real time monitoring of the treatment. Here, the device 100 can be coupled with a drill tool for removing the crown. Then, the drill tool is replaced with a suitable file, which is inserted into the treatment channel 40 so that the working end of the file is distally projecting into the root, and the file is used to excise the pulp material and to clean the dentine walls of the root. As more and more pulp is removed, the distal portion 30 of the device 100 is inserted deeper into the root. During all these operations the illumination channel 85 illuminates the interior surfaces of the tooth, and the light collection channel 95 picks up light reflected from these surfaces and displays the same in the optical display system 300, as described for the monitor mode, mutatis mutandis, allowing the user to ensure that the root is fully cleaned before progressing to the next step, and without the need for periodic x-rays, for example.

Figure 10A:
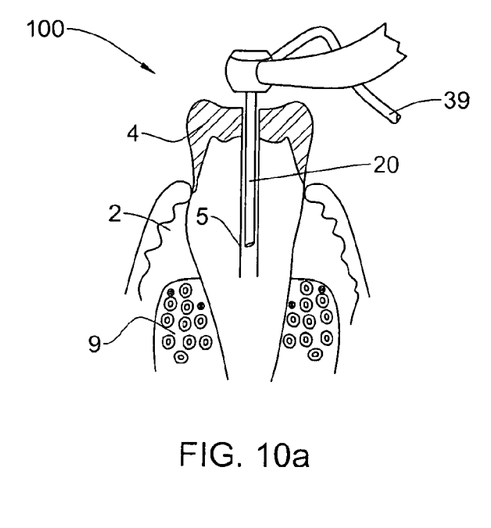
FIGS. 10a to 10c illustrate a use of a device according to an embodiment of the invention.
Figure 10B:
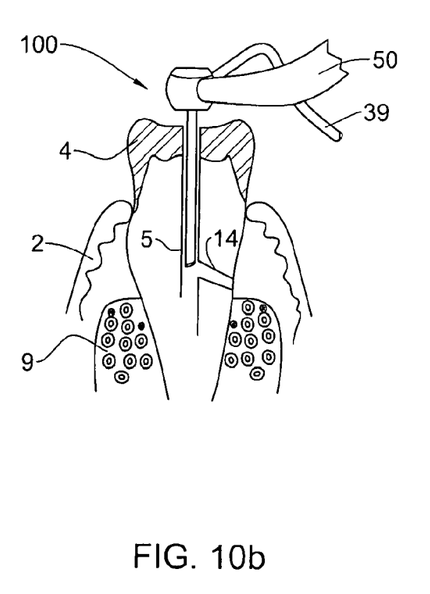
Figure 10C:
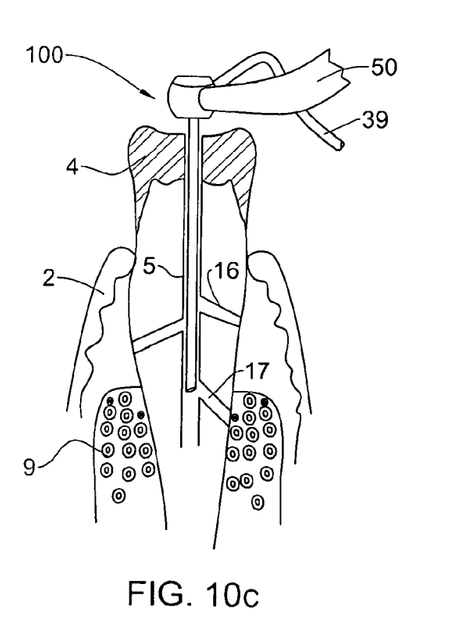

Alternatively, the root may be prepared using an ultrasonic tool, or a RHF tool, or a laser tool, and so on. Referring to FIGS. 10a to 10c, operation of device 100 using a laser tool is illustrated, in which FIG. 10a illustrates a cross sectional view of the dental area being treated, comprising crown 4 and root canal 5, seating in a lower gum bone 9 and margined by gums 2. The probe member 20 of the device 100 is inserted into the root canal 5. The provision of the monitoring or imaging channel in close proximity to the treatment tool, allows for directing the treatment laser radiation to a specific region inside the root canal. For example, as illustrated in FIG. 10b, such monitoring enables identification of a side root canal 14 to thereby allow a dentist to manipulate the device 100, in particular the probe member 20 that carries the laser treatment tool, which may have a wedge shaped distal end to direct the treatment radiation into canal 14. As shown in the example of FIG. 10c, the laser treatment tool carried in the treatment channel may be appropriately manipulated, as a result of the imaging provided by the device, to direct light to main canal 5 and side canals 16 and 17.

During such operations, the canal may be rinsed and drained using the auxiliary channel 35 and source 400.

Once the root has been cleaned out to the satisfaction of the dentist, the root may be sealed and filled. For this purpose, the tool that has been used for preparing the root canal is removed, and a suitable sealant, such as for example epoxy resins, zinc oxide eugenol, calcium hydroxide, and so on, may be injected into the root canal via the treatment channel 40. For this purpose, a syringe needle accommodated in the treatment channel may be used for example, the needle being coupled to a syringe containing the sealing agent. Then, a suitable filler, such as for example warmed gutta percha or Resilon may be injected into the root canal in a similar manner to that described for the sealant, mutatis mutandis. The sealant and/or filler may be self curing or may require light curing. In the latter case, the illumination system 200 may be configured for providing illumination light of the appropriate wavelength for this curing. During the sealing and filling operations, the user is able to monitor these activities, and adjust the same if necessary.

If necessary, a suitable antiseptic may be provided to the root canal via the treatment channel, prior to sealing and filling.

Other root canal procedures are also possible to perform using the device 100. For example, it may be possible to conduct an apicoectomy procedure via the root canal that has been previously prepared, for example as described above, mutatis mutandis. Then, a suitable laser tool or other electrosurgery tool, such as for example an RHF cutting tool, is coupled to the device 100, which is inserted into the root canal until the working distal end of the tool is close to the dental tissues around the apex 7 of the root. The tool can then be operated to cauterize the tissues, and the insertion and alignment of the tool, and operation thereof, may be monitored and control via the monitoring capabilities of the device 100. Similarly, the user can inspect the root tip to ensure that it has been fully treated before sealing and filling the root.

The device and system of the invention may also be used for other dental procedures. For example, the device and system may be used for carrying out procedures relating to periodontal pockets in the gingival tissues, and allow for exploration and/or treatment of the periodontal pockets by means of the monitoring and/or treatment capabilities thereof. The illumination channel and the light collection channel may be used for obtaining images of the periodontal pockets, and the treatment channel for providing irrigation thereto, or indeed for providing any other suitable treatment therethrough.

It should be understood that the present invention provides, if desired (based on the imaging) for appropriately manipulating (redirecting) the treatment tool (e.g., laser beam) while inside the root canal. Moreover, the use of the laser-based treatment allows for carrying out the entire root canal treatment (i.e., removing hard tissues inside the root canal) and the canal disinfection procedure.

In the method claims that follow, alphanumeric characters and Roman numerals used to designate claim steps are provided for convenience only and do not imply any particular order of performing the steps.

Finally, it should be noted that the word "comprising" as used throughout the appended claims is to be interpreted to mean "including but not limited to".

While there has been shown and disclosed example embodiments in accordance with the invention, it will be appreciated that many changes may be made therein without departing from the spirit of the invention.

The invention claimed is:

1. A device for use in a root canal treatment, the device comprising:
   a probe member and a handpiece for holding said elongate probe member, said probe member having an elongate distal portion capable of being accommodated in a root canal, said probe member comprising:
      at least one treatment channel having a distal opening in said elongate distal portion, said at least one treatment channel being configured for enabling operation of a suitable root canal treatment tool via said distal opening, such that in operation of the device, a working portion of said tool projects distally from a distal end of said distal portion, the working portion configured for operating within the root canal wherein to excise pulp material from the root canal responsive to operation of the tool;
      at least one illumination channel, different from said at least one treatment channel, and comprising a first light guide having a first proximal end configured for optical coupling to a light source system, and a second distal end in said distal portion for illuminating internal regions of the root canal during operation of said device;

at least one light collection channel comprising a second light guide having a first proximal end configured for optical coupling to an imaging system, and a second distal end located in said distal portion for collecting and transmitting light reflected from internal regions of the root canal to said proximal end during operation of said device;

wherein said device is configured for operation of the tool in the root canal concurrently with providing illumination to the root canal to enable monitoring of the treatment by said tool;

wherein said elongate distal portion comprises a length dimension along an elongate direction generally correlated with a depth of a root canal;

wherein said treatment channel comprises a suitable bore adapted for accommodating and enabling operation of a laser tool; and wherein said treatment channel comprises said laser tool, accommodated in said bore.

2. A device according to claim 1, wherein said length dimension is between about 10 mm and about 30 mm.

3. A device according to claim 1, wherein said elongate distal portion comprises a distal tip having a transverse dimension in a direction orthogonal to said elongate direction generally smaller than a width of a root canal at the apex thereof.

4. A device according to claim 3, wherein said elongate distal portion comprises a transverse dimension that is generally uniform along said elongate dimension thereof.

5. A device according to claim 4, wherein said transverse dimension is between about 500 micron and about 1500 micron.

6. A device according to claim 3, wherein said elongate distal portion comprises a transverse dimension that varies along said elongate dimension thereof.

7. A device according to claim 3, wherein said distal opening, said distal end of said first light guide, and said distal end of said second light guide are at or proximate to said distal tip.

8. A device according to claim 3, wherein said elongate distal portion has an enlarged portion proximately spaced from said tip by a first spacing.

9. A device according to claim 8, wherein said first spacing comprises a length dimension along an elongate direction generally correlated with between about 50% and about 70% of a depth of a root canal including the tip thereof.

10. A device according to claim 8, wherein said distal opening and said distal end of said first light guide are at or proximate to said distal tip, and wherein said distal end of said second light guide is comprised in said enlarged portion.

11. A device according to claim 8, wherein said distal opening is at or proximate to said distal tip, and wherein said distal end of said first light guide and said distal end of said second light guide are comprised in said enlarged portion.

12. A device according to claim 1, wherein said treatment channel is substantially rectilinear and comprises a proximal opening in said device substantially longitudinally opposed to said distal opening.

13. A device according to claim 1, further comprising said light source system optically coupled to said first light guide.

14. A device according to claim 13, wherein said light source system comprises at least one LED.

15. A device according to claim 1, wherein said first light guide comprises at least one of: at least one optical fiber; any suitable optical waveguide arrangement.

16. A device according to claim 1, further comprising said imaging system optically coupled to said second light guide.

17. A device according to claim 16, wherein said imaging system comprises a CCD in optical communication with said distal end of said second light guide via a system of lenses.

18. A device according to claim 17, wherein said CCD is operatively connectable to a microprocessor unit adapted for processing images transmitted thereto by said CCD.

19. A device according to claim 17, wherein said second light guide comprises an optical folding member.

20. A device according to claim 1, wherein said second light guide comprises at least one optical fiber.

21. A device according to claim 1, further comprising at least one auxiliary channel having a first proximal end configured for operative connection to at least one of a fluid source and a vacuum source, and a second distal end in said distal portion for providing fluid or a vacuum, respectively, to internal regions of the root canal during operation of said device.

22. A device according to claim 21, wherein said fluid source comprises any one of a liquid or air source.

23. A device according to claim 1, wherein said handpiece comprises a longitudinal axis set an angle alpha ($\alpha$) with respect to a longitudinal axis of said probing member.

24. A device according to claim 2, wherein said angle alpha ($\alpha$) is between about 45° and about 135°.

25. A device for use in a root canal treatment, the device comprising:

a probe member and a handpiece for holding said elongate probe member, said probe member having an elongate distal portion capable of being accommodated in a root canal, said probe member comprising:

at least one treatment channel having a distal opening in said elongate distal portion, said at least one treatment channel being configured for enabling operation of a suitable root canal treatment tool via said distal opening, such that in operation of the device, a working portion of said tool projects distally from a distal end of said distal portion, the working portion configured for operating within the root canal wherein to excise pulp material from the root canal responsive to operation of the tool;

at least one illumination channel, different from said at least one treatment channel, and comprising a first light guide having a first proximal end configured for optical coupling to a light source system, and a second distal end in said distal portion for illuminating internal regions of the root canal during operation of said device;

at least one light collection channel comprising a second light guide having a first proximal end configured for optical coupling to an imaging system, and a second distal end located in said distal portion for collecting and transmitting light reflected from internal regions of the root canal to said proximal end during operation of said device;

wherein said device is configured for operation of the tool in the root canal concurrently with providing illumination to the root canal to enable monitoring of the treatment by said tool;

wherein said elongate distal portion comprises a length dimension along an elongate direction generally correlated with a depth of a root canal;

wherein said treatment channel comprises a suitable bore adapted for accommodating and enabling operation of any one of: a dental drill, a dental file, a reaming tool; and wherein said treatment channel comprises any one of said dental drill, said dental file, said reaming tool, accommodated in said bore.

26. A device according to claim 25, wherein said elongate distal portion length dimension is between about 10 mm and about 30 mm.

27. A device according to claim 25, wherein said elongate distal portion comprises a distal tip having a transverse dimension in a direction orthogonal to said elongate direction generally smaller than a width of a root canal at the apex thereof.

28. A device according to claim 27, wherein said elongate distal portion comprises a transverse dimension that is generally uniform along said elongate dimension thereof.

29. A device according to claim 28, wherein said transverse dimension is between about 500 micron and about 1500 micron.

30. A device according to claim 27, wherein said elongate distal portion comprises a transverse dimension that varies along said elongate dimension thereof.

31. A device according to claim 27, wherein said distal opening, said distal end of said first light guide, and said distal end of said second light guide are at or proximate to said distal tip.

32. A device according to claim 27, wherein said elongate distal portion has an enlarged portion proximately spaced from said tip by a first spacing.

33. A device according to claim 32, wherein said first spacing comprises a length dimension along an elongate direction generally correlated with between about 50% and about 70% of a depth of a root canal including the tip thereof.

34. A device according to claim 32, wherein said distal opening and said distal end of said first light guide are at or proximate to said distal tip, and wherein said distal end of said second light guide is comprised in said enlarged portion.

35. A device according to claim 32, wherein said distal opening is at or proximate to said distal tip, and wherein said distal end of said first light guide and said distal end of said second light guide are comprised in said enlarged portion.

36. A device according to claim 25, wherein said treatment channel is substantially rectilinear and comprises a proximal opening in said device substantially longitudinally opposed to said distal opening.

37. A device according to claim 25, further comprising said light source system optically coupled to said first light guide.

38. A device according to claim 37, wherein said light source system comprises at least one LED.

39. A device according to claim 26, wherein said first light guide comprises at least one of: at least one optical fiber, and any suitable optical waveguide arrangement.

40. A device according to claim 26, wherein said imaging system is optically coupled to said second light guide.

41. A device according to claim 40, wherein said imaging system comprises a CCD in optical communication with said distal end of said second light guide via a system of lenses.

42. A device according to claim 41, wherein said CCD operatively connectable to a microprocessor unit adapted for processing images transmitted thereto by said CCD.

43. A device according to claim 41, wherein said second light guide comprises an optical folding member.

44. A device according to claim 26, wherein said second light guide comprises at least one optical fiber.

45. A device according to claim 25, further comprising at least one auxiliary channel having a first proximal end configured for operative connection to at least one of a fluid source and a vacuum source, and a second distal end in said distal portion for providing fluid or a vacuum, respectively, to internal regions of the root canal during operation of said device.

46. A device according to claim 45, wherein said fluid source comprises any one of a liquid or air source.

47. A device according to claim 25, wherein said handpiece comprises a longitudinal axis set an angle alpha ($\alpha$) with respect to a longitudinal axis of said probing member.

48. A device according to claim 47, wherein said angle alpha ($\alpha$) is between about 45° and about 135°.

49. A system for root canal treatment, comprising
a device comprising a probe member and a handpiece for holding said elongate probe member, said probe member having an elongate distal portion capable of being accommodated in a root canal, said probe member comprising:
at least one treatment channel having a distal opening in said elongate distal portion, said at least one treatment channel being configured for enabling operation of a suitable root canal treatment tool via said distal opening;
at least one illumination channel, different from said at least one treatment channel, and comprising a first light guide having a first proximal end configured for optical coupling to a light source system, and a second distal end in said distal portion for illuminating internal regions of the root canal during operation of said device;
at least one light collection channel comprising a second light guide having a first proximal end configured for optical coupling to an imaging system, and a second distal end located in said distal portion for collecting and transmitting light reflected from internal regions of the root canal to said proximal end during operation of said device;
a light source system coupled to said proximal end of said first light guide;
an imaging system coupled to said proximal end of said second light guide; and
a root canal treatment tool comprised in said treatment channel, said tool having a treating portion projecting distally from said distal outlet and configured for operating within the root canal, said tool comprising any one of a dental drill, a dental file, and a reaming tool;
wherein said system is configured for operation of the tool in the root canal concurrently with providing illumination to the root canal to enable monitoring of the treatment by said tool.

50. A system for root canal treatment, comprising
a device comprising a probe member and a handpiece for holding said elongate probe member, said probe member having an elongate distal portion capable of being accommodated in a root canal, said probe member comprising:
at least one treatment channel having a distal opening in said elongate distal portion, said at least one treatment channel being configured for enabling operation of a suitable root canal treatment tool via said distal opening;
at least one illumination channel, different from said at least one treatment channel, and comprising a first light guide having a first proximal end configured for optical coupling to a light source system, and a second distal end in said distal portion for illuminating internal regions of the root canal during operation of said device;
at least one light collection channel comprising a second light guide having a first proximal end configured for optical coupling to an imaging system, and a second distal end located in said distal portion for collecting and transmitting light reflected from internal regions of the root canal to said proximal end during operation of said device;

a light source system coupled to said proximal end of said first light guide;

an imaging system coupled to said proximal end of said second light guide; and a root canal treatment tool comprised in said treatment channel, said tool having a treating portion projecting distally from said distal outlet and configured for operating within the root canal wherein to excise pulp material from the root canal responsive to operation of the tool, said tool comprising a laser tool;

wherein said device is configured for operation of the tool in the root canal concurrently with providing illumination to the root canal to enable monitoring of the treatment by said tool.

51. A system according to claim 50, wherein said tool is a laser tool having a laser transmission end adapted for any one of axial transmission of a laser beam and non-axial transmission of a laser beam, with respect to a longitudinal axis of said elongate distal portion.

52. A system for root canal treatment, comprising:

a device comprising a probe member and a handpiece for holding said elongate probe member, said probe member having an elongate distal portion capable of being accommodated in a root canal, said probe member comprising:

at least one treatment channel having a distal opening in said elongate distal portion, said at least one treatment channel being configured for enabling operation of a suitable root canal treatment tool via said distal opening;

at least one illumination channel, different from said at least one treatment channel, and comprising a first light guide having a first proximal end configured for optical coupling to a light source system, and a second distal end in said distal portion for illuminating internal regions of the root canal during operation of said device;

at least one light collection channel comprising a second light guide having a first proximal end configured for optical coupling to an imaging system, and a second distal end located in said distal portion for collecting and transmitting light reflected from internal regions of the root canal to said proximal end during operation of said device;

a light source system coupled to said proximal end of said first light guide;

an imaging system coupled to said proximal end of said second light guide; and a root canal treatment tool comprised in said treatment channel, said tool having a treating portion projecting distally from said distal outlet and configured for operating within the root canal, said tool comprising a syringe needle coupled to at least one of a source of filling agent and a source of sealing agent for respectively filling or sealing a root canal during operation of the device;

wherein said device is configured for operation of the tool in the root canal concurrently with providing illumination to the root canal to enable monitoring of the treatment by said tool.

53. A method for monitoring a root canal treatment, comprising:

illuminating the root canal with an illumination radiation and acquiring at least one image of said root canal illuminated thereby, while concurrently operating a mechanical or laser tool to perform the root canal treatment, wherein said illumination and said image acquisition are carried out by means of a suitable probe member inserted into said root canal, and further comprising using a system for root canal treatment comprising:

a device comprising a probe member and a handpiece for holding said elongate probe member, said probe member having an elongate distal portion capable of being accommodated in a root canal, said probe member comprising:

at least one treatment channel having a distal opening in said elongate distal portion, said at least one treatment channel being configured for enabling operation of a suitable root canal treatment tool via said distal opening;

at least one illumination channel, different from said at least one treatment channel, and comprising a first light guide having a first proximal end configured for optical coupling to a light source system, and a second distal end in said distal portion for illuminating internal regions of the root canal during operation of said device;

at least one light collection channel comprising a second light guide having a first proximal end configured for optical coupling to an imaging system, and a second distal end located in said distal portion for collecting and transmitting light reflected from internal regions of the root canal to said proximal end during operation of said device;

a light source system coupled to said proximal end of said first light guide;

an imaging system coupled to said proximal end of said second light guide; and a root canal treatment tool comprised in said treatment channel, said tool having a treating portion projecting distally from said distal outlet and configured for operating within the root canal, said tool comprising any one of a dental drill, a dental file, an ultrasonic tool, an RHF cutting tool, a reaming tool, and a grasping tool;

wherein said system is configured for operation of the tool in the root canal concurrently with providing illumination to the root canal to enable monitoring of the treatment by said tool.

54. A method according to claim 53, wherein a plurality of images is acquired to provide a video stream in real time.

55. A method for treating a root canal, comprising illuminating the root canal with an illumination radiation and acquiring at least one image of said root canal illuminated thereby; and performing a root canal treatment: wherein said image acquisition is carried out while performing a root canal treatment; further comprising using a system for root canal treatment, comprising a device comprising a probe member and a handpiece for holding said elongate probe member, said probe member having an elongate distal portion capable of being accommodated in a root canal, said probe member comprising: at least one treatment channel having a distal opening in said elongate distal portion, said at least one treatment channel being configured for enabling operation of a suitable root canal treatment tool via said distal opening; at least one illumination channel, different from said at least one treatment channel, and comprising a first light guide having a first proximal end configured for optical coupling to a light source system, and a second distal end in said distal portion for illuminating internal regions of the root canal during operation of said device; at least one light collection channel comprising a second light guide having a first proximal end configured for optical coupling to an imaging system, and a second distal end located in said distal portion for collecting and transmitting light reflected from internal regions of the root canal to said proximal end during operation of said device; a light source system coupled to said proximal end of said first light guide; an imaging system coupled to said proximal end of said second light guide; and a root canal treatment tool comprised in said treatment channel, said tool having a treating portion projecting distally from said distal outlet and configured for operating within the root canal, said tool comprising any one of a dental drill, a dental file, and a reaming tool; wherein said system is configured for operation of the tool in the root canal concurrently with providing illumination to the root canal to enable monitoring of the treatment by said tool.

56. A method according to claim 55, wherein said root canal treatment comprises one of a sealing or filing procedure for the root canal.

57. A method according to claim 56, wherein said one of a sealing or filing procedure comprises injecting a suitable sealant or filler, respectively, to the root canal via said treatment channel.

58. A system for root canal treatment, comprising:
- a device comprising a probe member and a handpiece for holding said elongate probe member, said probe member having an elongate distal portion capable of being accommodated in a root canal, said probe member comprising:
- at least one treatment channel having a distal opening in said elongate distal portion, said at least one treatment channel being configured for enabling operation of a suitable root canal treatment tool via said distal opening;
- at least one illumination channel, different from said at least one treatment channel, and comprising a first light guide having a first proximal end configured for optical coupling to a light source system, and a second distal end in said distal portion for illuminating internal regions of the root canal during operation of said device;
- at least one light collection channel comprising a second light guide having a first proximal end configured for optical coupling to an imaging system, and a second distal end located in said distal portion for collecting and transmitting light reflected from internal regions of the root canal to said proximal end during operation of said device;
- a light source system coupled to said proximal end of said first light guide;
- an imaging system coupled to said proximal end of said second light guide; and
- a root canal treatment tool comprised in said treatment channel, said tool having a treating portion projecting distally from said distal outlet and configured for operating within the root canal, said tool comprising any one of an ultrasonic tool, an RHF cutting tool, and a grasping tool;
- wherein said system is configured for operation of the tool in the root canal concurrently with providing illumination to the root canal to enable monitoring of the treatment by said tool.

* * * * *